(12) United States Patent
Housey et al.

(10) Patent No.: US 8,557,512 B2
(45) Date of Patent: Oct. 15, 2013

(54) METHOD OF SCREENING ACTIVATORS AND/OR INHIBITORS OF INSULIN RECEPTOR SUBSTRATE 2

(75) Inventors: Gerard M. Housey, Southfield, MI (US); Morris F. White, Norwood, MA (US)

(73) Assignee: HMI Medical Innovations, LLC, Southfield, MI (US)

( * ) Notice: Subject to any disclaimer, the term of this patent is extended or adjusted under 35 U.S.C. 154(b) by 393 days.

(21) Appl. No.: 10/541,263

(22) PCT Filed: Dec. 31, 2003

(86) PCT No.: PCT/US03/41745
§ 371 (c)(1),
(2), (4) Date: Apr. 18, 2006

(87) PCT Pub. No.: WO2004/060316
PCT Pub. Date: Jul. 22, 2004

(65) Prior Publication Data
US 2006/0241030 A1     Oct. 26, 2006

Related U.S. Application Data

(60) Provisional application No. 60/437,377, filed on Jan. 2, 2003.

(51) Int. Cl.
*C12Q 1/00* (2006.01)
*C12N 5/00* (2006.01)
*C12N 5/07* (2010.01)
*C12N 15/64* (2006.01)
*C12N 15/87* (2006.01)

(52) U.S. Cl.
USPC ............... 435/4; 435/7.8; 435/336; 435/91.4; 435/462; 435/463; 435/477

(58) Field of Classification Search
None
See application file for complete search history.

(56) References Cited

U.S. PATENT DOCUMENTS

| | | |
|---|---|---|
| 5,260,200 A | 11/1993 | Kahn et al. |
| 5,688,655 A | 11/1997 | Housey |
| 5,858,701 A | 1/1999 | White et al. |
| 2001/0012829 A1 | 8/2001 | Anderson et al. |
| 2002/0098169 A1 | 7/2002 | Smith |

FOREIGN PATENT DOCUMENTS

DE     19921537 A1     11/2000

OTHER PUBLICATIONS

Definition of "regulatory sequence", from Principles of Biochemistry, 2nd Ed., Lehninger, 1993; p. G-13 (3 pages total).*
Aguirre et al., Phosphorylation of Ser307 in insulin receptor substrate-1 blocks interactions with the insulin receptor and inhibits insulin action. J Biol Chem. Jan. 11, 2002;277(2):1531-7. Epub Oct. 17, 2001.
Dachicourt, N. et al., Glucagon-like peptide-1 (7-36)-amide confers glucose sensitivity to previously glucose-incompetent β-cells in diabetic rats: in vivo and in vitro studies. J. of Endocrinology 1997, vol. 155, pp. 369-376.
Drucker, D. J., Development of glucagon-like peptide-1-based pharmaceuticals as therapeutic agents for the treatment of diabetes, Current Pharmaceutical Design, 2001, vol. 7, pp. 1399-1412.
Frasca et al., Insulin receptor isoform A, a newly recognized, high-affinity insulin-like growth factor II receptor in fetal and cancer cells. Mol Cell Biol. May 1999;19(5):3278-88.
Fruebis et al., Proteolytic cleavage product of 30-kDa adipocyte complement-related protein increases fatty acid oxidation in muscle and causes weight loss in mice. Proc Natl Acad Sci U S A. Feb. 13, 2001;98(4):2005-10. Epub Feb. 6, 2001.
Haj et al., Imaging sites of receptor dephosphorylation by PTP1B on the surface of the endoplasmic reticulum. Science. Mar. 1, 2002;295(5560):1708-11.
Hennige, A. M., et al., Upregulation of insulin receptor substrate-2 in pancreatic β cells prevents diabetes, J. Clin. Invest. 2003, vol. 112:10, 1521-1532.
Hotamisligil et al., Adipose expression of tumor necrosis factor-alpha: direct role in obesity-linked insulin resistance.Science. Jan. 1, 1993;259(5091):87-91.
Hotamisligil et al., IRS-1-mediated inhibition of insulin receptor tyrosine kinase activity in TNF-alpha- and obesity-induced insulin resistance. Science. Feb. 2, 1996;271(5249):665-8.
Jhala, U. S., et al., cAMP promotes pancreatic β-cell survival via CREB-mediated induction of IRS2, Genes & Dev. 2003, vol. 17, pp. 1575-1580.
Kitamura et al., The forkhead transcription factor Foxo1 links insulin signaling to Pdx1 regulation of pancreatic beta cell growth. J Clin Invest. Dec. 2002;110(12):1839-47.
Krebs, D. L., et al., A new role for SOCS in insulin action. Sci STKE 2003 (169), pe6. (http://stke.sciencemag.org/cgi/cm/CMP_12069).
Nakae et al., The forkhead transcription factor Foxo1 regulates adipocyte differentiation. Dev Cell. Jan. 2003;4(1):119-29.

(Continued)

*Primary Examiner* — Bridget E Bunner
*Assistant Examiner* — Christina Borgeest
(74) *Attorney, Agent, or Firm* — Kenyon & Kenyon LLP

(57) ABSTRACT

This invention is directed to a general method for the chronic treatment, potential cure, or prevention of various metabolic and related diseases in people, including diabetes, by modulating IRS2 activity in cells and tissues in the body. IRS1 and IRS2 are part of the insulin or insulin-like growth factor signaling pathway. By upregulating the levels or functional activity of IRS2, insulin is used more efficiently by the body to control nutrient levels. By upregulating IRS2 levels or functional activity in pancreatic β-cells, glucose sensing and insulin secretion are enhanced.

9 Claims, 2 Drawing Sheets

(56) References Cited

OTHER PUBLICATIONS

Ogg et al. The Fork head transcription factor DAF-16 transduces insulin-like metabolic and longevity signals in *C. elegans*. Nature. Oct. 30, 1997;389(6654):994-9.

Peraldi et al., Tumor necrosis factor (TNF)-alpha inhibits insulin signaling through stimulation of the p55 TNF receptor and activation of sphingomyelinase. J Biol Chem. May 31, 1996;271(22):13018-22.

Puigserver et al., Insulin-regulated hepatic gluconeogenesis through FOXO1-PGC-1alpha interaction. Nature. May 29, 2003;423(6939):550-5. Epub May 18, 2003.

Savkur et al., Aberrant regulation of insulin receptor alternative splicing is associated with insulin resistance in myotonic dystrophy. Nat Genet. Sep. 2001;29(1):40-7.

Shaw et al., Identification of insulin receptor substrate 1 (IRS-1) and IRS-2 as signaling intermediates in the alpha6beta4 integrin-dependent activation of phosphoinositide 3-OH kinase and promotion of invasion. Mol Cell Biol. Aug. 2001;21(15):5082-93.

Sun et al., Role of IRS-2 in insulin and cytokine signaling. Nature. Sep. 14, 1995;377(6545):173-7.

Sun et al., Structure of the insulin receptor substrate IRS-1 defines a unique signal transduction protein Nature. Jul. 4, 1991;352(6330):73-7.

Trumper, K. et al. Integrative mitogenic role of protein kinase B/Akt in β-cells, Ann. NY Acad. Sci. 2000, vol. 921, pp. 242-250.

White et al., Insulin rapidly stimulates tyrosine phosphorylation of a Mr-185,000 protein in intact cells. Nature. Nov. 14-20, 1985;318(6042):183-6.

Withers et al., Disruption of IRS-2 causes type 2 diabetes in mice. Nature. Feb. 26, 1998;391(6670):900-4.

Yenush et al., Tthe pleckstrin homology and phosphotyrosine binding domains of insulin receptor substrate 1 mediate inhibition of apoptosis by insulin. Mol Cell Biol. Nov. 1998;18(11):6784-94.

Yuan et al., Reversal of obesity- and diet-induced insulin resistance with salicylates or targeted disruption of Ikkbeta. Science. Aug. 31, 2001;293(5535):1673-7.

Zimmet et al., Global and societal implications of the diabetes epidemic. Nature. Dec. 13, 2001;414(6865):782-7.

Burks, D.J. et al., IRS-2 pathways integrate female reproduction and energy homeostasis. Nature, vol. 407, Sep. 21, 2000, pp. 377-382.

Greig, N.II. et al., Once daily injection of exendin-4 to diabetic mice achieves long-term beneficial effects on blood glucose concentrations. Diabetologia, (1999) vol. 42, pp. 45-50.

Perry, T.A. et al., The glucagon-like peptides: a new genre in therapeutic targets for intervention in Alzheimer's disease. Journal of Alzheimer's Disease (2002) vol. 4, pp. 487-496.

Vaβen, L. et al. Human Insulin Receptor Substrate-2. Diabetes, vol. 48, Sep. 1999, pp. 1877-1880.

Zander, M. et al., Effect of 6-week course of glucagon-like peptide 1 on glycaemic control, insulin sensitivity, and β-cell function in type 2 diabetes: a parallel-group study, The Lancet, vol. 359 Mar. 9, 2002, pp. 824-830.

Li L. et al., "Overexpression of Insulin Receptor Substrate -1, but not Insulin receptor Substrate-2, protects a T Cell Hybridoma from activiation-induced cell death". The Journal of Immunology, (2002) vol. 168, pp. 6215-6223.

Vassen, L. et al., "Human insulin receptor substrate-2 (IRS-2) is a primary progesterone response gene". Molecular Endocrinology (1999), vol. 13, pp. 485-494.

Zhou, L. et al., "Insulin receptor substrate-2 (IRS-20 can mediate the action of insulin to stimulate translocation of GLUT4 to the cell surface in rat adipose cells". Journal of Biological Chemistry, (Nov. 21, 1997), vol. 272:47 pp. 29829-29833.

\* cited by examiner

METHOD OF SCREENING ACTIVATORS AND/OR INHIBITORS OF INSULIN RECEPTOR SUBSTRATE 2

CROSS-REFERENCE TO RELATED APPLICATION

This application claims priority to U.S. provisional application 60/437,377 filed on Jan. 2, 2003, incorporated by reference herein.

FIELD OF THE INVENTION

This is a general method for the prevention, induction of long term remission, or even the cure of various metabolic diseases and disorders in human beings and animals, including type 2 diabetes, by regulating the IRS2/IRS1 levels and signaling function in cells and tissues in the body. IRS1 and IRS2 are part of the insulin or insulin like growth factor signaling pathways, but also mediate some signals through other growth factors and cytokines, including IFNγ, IL2, IL4, IL7, IL9, IL13 or IL15, growth hormone, prolactin, or leptin. IRS1 or IRS2 functional activity also integrate signals emanating from proinflammatory cytokines, including TNFα, IL6, IL1β and related factors. In general proinflammatory cytokines inhibit IRS1/IRS2 signaling which might contribute to insulin resistance syndromes.

BACKGROUND OF THE INVENTION

Diabetes mellitus is a complex and life threatening disease that has been known for more than 2000 years. It occurs in mammals as diverse as monkeys, dogs, rats, mice and human beings. The discovery of insulin and its purification in 1921 for use in people provided a partial treatment for diabetes that is still in widespread use today. Insulin levels are ordinarily adjusted by the body on a moment to moment basis to keep the blood sugar level within a narrow physiological range. Periodic insulin injections, however, can only approximate the normal state because the cellular response to insulin in many cases is also reduced. Consequently, for these and other reasons which will be discussed in detail below, life threatening complications still occur during the lifetime of treated diabetic patients, especially in the case of type 2 (adult-onset) diabetes.

Diabetes arises from various causes, including dysregulated glucose sensing or insulin secretion (Maturity onset diabetes of youth; MODY), autoimmune-mediated β-cell destruction (type 1), or insufficient compensation for peripheral insulin resistance (type 2). (Zimmet, P. et al., *Nature* 414:782-787 (2001)). Type 2 diabetes is the most prevalent form of the disease: It is closely associated with obesity, usually occurs at middle age, and afflicts 18.2 million Americans. The common mechanism causing peripheral insulin resistance and β-cell failure is important to understand.

Peripheral insulin resistance contributes to type 2 diabetes, but β-cell failure is an essential feature of all types of diabetes. β-cells frequently fail to compensate for insulin resistance, apparently because the IRS2-branch of the insulin and IGF signaling cascade which mediates insulin signaling in target tissues also is essential for β-cell growth, function and survival. (Withers, D. J. et al., *Nature* 391:900-904 (1998)).

Because insulin resistance is a cause of metabolic dysregulation and diabetes, understanding its molecular basis is an important goal. Genetic mutations are obvious sources of life-long insulin resistance, but they are associated with rare metabolic disorders and thus difficult to identify in the general population. Inflammation is associated with insulin resistance and provides a framework to understand how diet, acute or chronic stress, and obesity might cause insulin resistance. Proinflammatory cytokines, including IL6 and tumor necrosis factor-α (TNFα) that are secreted from leukocytes during inflammation, are also produced in adipose tissue. TNFα promotes serine phosphorylation of IRS-proteins, which correlates closely with insulin resistance. (Hotamisligil, G. S. et al., *Science* 259:87-91 (1999); Hotamisligil, G. S. et al., *Science* 271:665-668 (1996); Peraldi, P. et al., *J. Biol. Chem.* 271:13018-13022 (1996)). Although TNFα regulates various kinases, the $NH_2$-terminal Jun kinase (Jnk) is a prominent effector because it binds to IRS1 and IRS2 and phosphorylates serine residues that inhibit the interaction between IRS1 and the insulin receptor. (Aguirre, V. et al., *J. Biol. Chem.* 277:1531-1537 (2002)). The knockout of Jnk1 in obese mice, or general inhibition of serine kinases by high doses of salicylates reduces Ser phosphorylation of IRS1 and reverses hyperglycemia, hyperinsulinemia, dyslipidemia in obese rodents by sensitizing insulin signaling pathways. (Fruebis, J. et al., *Proc. Natl. Acad. Sci. U.S.A* 98:2005-2010 (2001); Yuan, M. et al., *Science* 293:1673-1677 (2001)).

Ubiquitin-mediated degradation of IRS-proteins also promotes insulin resistance (FIG. 1). IL6 secreted from leukocytes and adipocytes increases expression of SOCS1 and SOCS3, known for the ability to suppress cytokine signaling. Another function of SOCS1 and SOCS3 is to recruit an elongin BC-based ubiquitin ligase into the IRS-protein complex to mediate ubiquitinylation. Thus, ubiquitin-mediated degradation of IRS-proteins might be a general mechanism of cytokine-induced insulin resistance that contributes to diabetes or β-cell failure. (Krebs, D. L. et al., *Sci. STKE.* 2003, E6 (2003)). Modern genomic approaches have revealed new cytokines secreted directly from adipocytes that directly influence nutrient homeostasis and insulin sensitivity, including leptin, adiponectin, resistin and others that will reveal new mechanisms to modulate insulin sensitivity.

The activity of protein or lipid phosphatases, including PTP1B, SHIP2 or pTEN modulates insulin sensitivity (FIG. 1). Disruption of each of these genes in mice increases insulin sensitivity, suggesting that each might be a target for inhibitor design. PTP1B resides in the endoplasmic reticulum where it dephosphorylates the insulin receptor during internalization and recycling to the plasma membrane. (Haj, F. G. et al., *Science* 295:1708-1711 (2002)). This specialized mechanism appears to limit unwanted side effects associated with inhibition of phosphatases, including unregulated cell growth.

The insulin receptor is the prototype for a family of homologous integral membrane proteins composed of an extracellular insulin-binding domain that controls the activity of an intracellular tyrosine kinase. A 150-kb gene on chromosome 19 composed of 22 exons encodes the human proreceptor. During translation, two homologous proreceptors form a disulfide-linked dimer that is glycosylated and cleaved to form a heterotetramer of two extracellular α-subunits and two trans-membrane β-subunits. Insulin binds to the juxtaposed α-subunits facilitating ATP binding and tyrosine autophosphorylation of the β-subunit, which activates the kinase and recruits cellular substrates to initiate signal transduction. The full insulin-signaling pathway as presently known is summarized in the STKE Connections Map. (White, M., Insulin Signaling Pathway, Sci. STKE Connections Map, as seen November 2003, http://stke.sciencemag.org/cgi/cm/CMP_12069).

Selective insulin binding is complicated by tissue-specific alternative splicing that directs synthesis of two insulin receptor isoforms (IRa and IRb), and by post-translational assembly of hybrids between these isoforms and the homologous IGF1 receptor (IGF1R). (Frasca, F. et al., *Mol. Cell Biol.* 19:3278-3288 (1999)). IRb exclusively binds insulin, whereas IRa binds both insulin and IGF2 with similar affinities: Dysregulated splicing alters fetal growth patterns and contributes to rare forms of insulin resistance in adults. (Frasca, 1989; Savkur, R. S. et al., *Nat. Genet.* 29:40-47 (2001)) Moreover, hybrid receptors composed of an αβ-dimer from the IGF1R and the IRb selectively bind IGF1, whereas hybrid receptors composed of IGF1R and IRa bind IGFs and insulin with similar affinities (FIG. 1).

The first member of the insulin receptor substrate family of proteins was discovered in 1985, and subsequent research efforts revealed the existence of related IRS family members as well as the signaling pathways to which the IRS proteins are linked. After the discovery that the Insulin Receptor (IR) possessed a tyrosine kinase enzyme activity, many groups searched for insulin receptor substrates that might regulate downstream signaling from the receptor. The first evidence for the existence of an actual target protein for the Insulin Receptor, subsequently named an Insulin Receptor Substrate, or "IRS" protein, resulted from the use of phosphotyrosine antibody immunoprecipitates which surprisingly revealed a 185-kDa phosphoprotein (pp185) in insulin-stimulated hepatoma cells. (White, M. F. et al., *Nature* 318:183-186 (1985)). Purification and molecular cloning of pp185 revealed one of the first signaling scaffolds as well as the first Insulin Receptor Substrate protein (IRS1). (U.S. Pat. No. 5,260,200; Sun, X. J. et al., *Nature* 352:73-77 (1991)). IRS1 was determined to be biologically important because it was phosphorylated immediately after insulin stimulation, and catalytically active insulin receptor mutants that failed to phosphorylate IRS1 were biologically inactive. Most, if not all, insulin signals are produced or modulated through tyrosine phosphorylation of IRS1, IRS2 or its homologs; or other scaffold proteins including SHC, CBL, APS and SH2B, GAB1, GAB2, DOCK1, and DOCK2. Although the role of each of these substrates merits attention, work with transgenic mice suggests that many insulin responses, especially those that are associated with somatic growth and carbohydrate metabolism, are mediated through IRS1 or IRS2.

IRS-proteins are composed of multiple interaction domains and phosphorylation motifs, but appear to lack intrinsic catalytic activities. All IRS-proteins contain an $NH_2$-terminal pleckstrin homology (PH) domain adjacent to a phosphotyrosine-binding (PTB) domain, followed by a COOH-terminal tail with numerous tyrosine and serine phosphorylation sites. The PTB domain binds directly to the phosphorylated NPXY-motif—Asn-Pro-Xaa-Tyr(Pi), Xaa represents any amino acid—in the activated receptors for insulin, IGFs or interleukin-4 (IL4); the PH domain also couples IRS-proteins to activated receptors, but the mechanism is unclear. (Yenush, L. et al., *Mol. Cell Biol.* 18:6784-6794 (1998)). Other receptors also recruit and phosphorylate IRS-proteins, including those for growth hormone, IL-9, IL-13 and IL-15, and various integrins. (Shaw, L. M., *Mol. Cell Biol.* 21:5082-5093 (2001)).

Tyrosine phosphorylation sites in IRS1 and IRS2 bind common effector proteins, including enzymes (phosphoinositide 3-kinase, the phosphatase SHP2, or the tyrosine kinase fyn) or adapters (SOCS1, SOCS3, GRB2, NCK, CRK, SHB and others).

Activation of PI3K during association with IRS proteins increases the activity of protein kinase B (PKB), which phosphorylates various substrates including BAD (important for cell survival), GSK3β (regulating growth and glycogen synthesis), and Foxo1 (controlling gene expression) (FIG. 1). A role for Foxo1 in insulin or IGF action was revealed by mutations in the *C. elegans* ortholog Daf16. (Ogg, S. et al., *Nature* 389:994-999 (1997)). During insulin or IGF stimulation, Daf16 and Foxo1 are phosphorylated by PKB and accumulate in the cytosol. Nuclear exclusion of Foxo1 inhibits hepatic gluconeogenesis, but stimulates adipocyte differentiation and pancreatic β-cell function. (Nakae, J. et al., *Dev. Cell* 4:119-129 (2003); Kitamura, T. et al., *J. Clin. Invest* 110:1839-1847 (2002); Puigserver, P. et al., *Nature* 423:550-555 (2003)).

IRS1 contains many tyrosine phosphorylation sites that are phosphorylated during insulin and insulin-like growth factor 1 (IGF1) stimulation, and bind to the Src homology-2 domains in various signaling proteins. The interaction between IRS1 and p85 activates the class 1A phosphotidylinositide 3-kinase, thereby revealing the first insulin signaling cascade that could be reconstituted successfully in cells and test tubes.

Several experiments suggested that other related proteins might exist: IRS1 antibodies did not react completely with the phosphotyrosine containing protein that migrated at 185 kDa during SDS-PAGE; FDCP1 cells contained a protein with characteristics similar to those of IRS1 but failed to react with antibodies directed against IRS1; the liver of transgenic mice lacking IRS1 still contained a protein in liver that had characteristics of IRS1. All of these finding led to the purification and cloning of Insulin Receptor Substrate 2 (IRS2), a second member of the IRS family. (U.S. Pat. No. 5,858,701; Sun, X. J. et al., *Nature* 377:173-177 (1995)).

Experiments in transgenic mice revealed involvement of IRS1 and IRS2 in promoting somatic growth and nutrient homeostasis. Without IRS1, mice are 50% smaller than normal from birth until they die at 2 years of age. Mice without IRS1 have less body fat and are glucose intolerant. In mice, IRS2 is important for peripheral insulin action, as mice lacking IRS2 display glucose intolerance and hyperlipidemia.

Disruption of the IRS2 gene in mice using standard gene knockout approaches results in diabetes that develops during the first 10 to 12 weeks of age. Pancreatic β-cells are lost from these mice as they age, and genes that are important for β-cell function are down regulated in mice lacking IRS2.

SUMMARY OF THE INVENTION

It has now been discovered that a family of target proteins that function immediately downstream of the insulin receptor or insulin like growth factor receptors, termed the insulin receptor substrate (IRS) protein family, is of central importance in mediating the effects of insulin on responsive cells. In particular, up regulation of the level or functional activity of IRS2 in humans will result in a therapeutically effective chronic treatment for patients suffering from diabetes, especially the adult onset (type 2) form of the disease, as well as for other disorders in which IRS protein function is insufficient, abnormal or absent altogether. Further, IRS1 and IRS2 are of central importance in the insulin or insulin like growth factor signaling pathway, and also mediate signals by other growth factors and cytokines.

Accordingly, the invention is directed to a general method for the treatment, cure, or prevention of various metabolic and related disorders, including diabetes, by regulating the level or functional activity of IRS proteins.

In one embodiment, the invention is directed to restoring or enhancing insulin sensitivity in a cell by upregulating IRS2 function. The invention is further directed to enhancing pancreatic β-cell function by upregulating IRS2 function. According to the invention, a disease or disorder characterized by reduced or insufficient signaling through IRS2 can be treated by upregulating IRS2 function. Such diseases include, but are not limited to metabolic disease, diabetes, dyslipidemia, obesity, female infertility, central nervous system disorders, Alzheimer's disease, and disorders of angiogenesis.

According to the invention, upregulation of IRS2 function includes activation of IRS2 or a complex that includes IRS2. Upregulation of IRS2 function is also accomplished by inhibition of phosphorylation of carboxy terminal serine residues of IRS2. Upregulation of IRS2 function can be accomplished by enhanced expression of IRS2 or by inhibition of degradation of IRS2.

In another embodiment, the invention is directed to a method of determining whether a small molecule is an activator or an inhibitor of IRS2. In a cell-based assay, a Test Cell is provided which overproduces IRS2 and exhibits an increase in binding of an IRS2-binding protein to IRS2, relative to a Control cell which produces IRS2 at a lower level, or does not produce the protein at all, and which exhibits a lesser amount of binding of said protein to IRS2. Small molecules that activate or inhibit IRS2 are identified by measuring the amount of the IRS2 binding protein bound to IRS2.

In another embodiment, the invention is directed to a method of identifying a small molecule capable of increasing the level of expression from an IRS2 promoter in a mammalian cell. In one such embodiment, a Test Cell is constructed which contains a construct comprising an IRS2 promoter operably linked to a reporter gene such that increased expression of the IRS2 promoter sequence using a substance known to be capable of upregulating the endogenous IRS2 gene results in an increase in said measurable characteristic of the Test cell. Small molecules that increase IRS2 expression are identified by detecting an increase in reporter gene activity.

DETAILED DESCRIPTION

Figure 1:
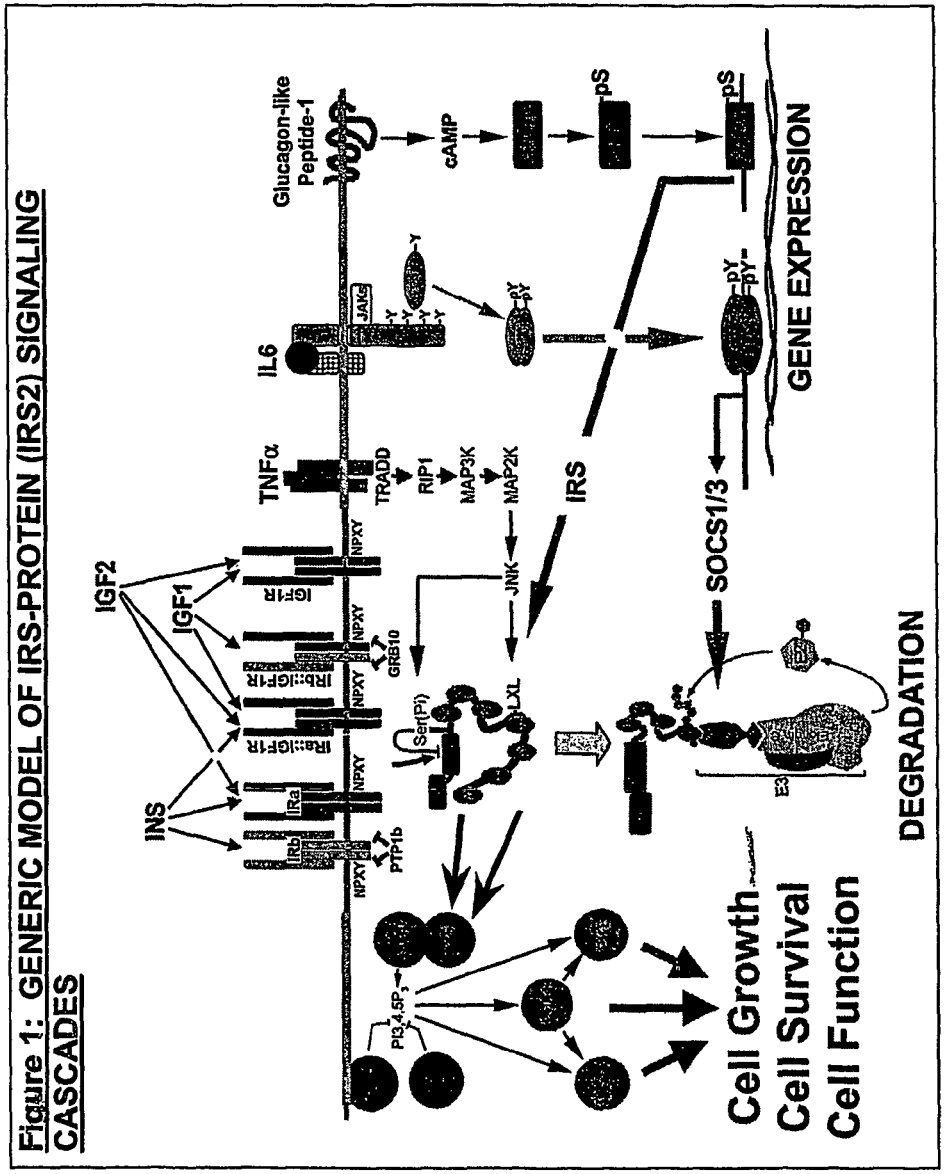
FIG. 1 depicts components of the IRS signaling cascade.

This invention pertains to generalized methods of preventing, curing or inducing durable long-term remissions in patients with diabetes, metabolic disorders, central nervous system diseases, obesity, fertility and other human disorders in which an inappropriate level of functional cellular activity of the IRS family of proteins contribute to the disease state. The invention is particularly concerned with IRS2 and modulation of the activity of IRS2-mediated cellular signaling pathways as a mechanism for treating human disease.

The invention is based on the recognition that the IRS2 branch of the insulin/IGF signaling system coordinates important biochemical reactions and signaling pathways needed for proper function of peripheral insulin sensitive tissues and cells (liver muscle and fat), the function of components in the brain that coordinate nutrient homeostasis and appetite regulation (hypothalamus), pancreatic beta cells that sense glucose and secrete insulin, and in the reproductive system.

Experiments in genetically altered mice that lack IRS2 or overexpress IRS2 reveal the essential role for IRS2 in peripheral insulin action and the role of IRS2 in the function, growth and survival of pancreatic β-cells. In mice, IRS2 is important for peripheral insulin action, pancreatic beta cell glucose sensing and insulin secretion, and CNS control of nutrient homeostasis that regulates appetite and obesity. Dysregulation of IRS2 signaling in peripheral insulin sensitive tissues, pancreatic beta cells and brain causes insulin resistance, β-cell failure and obesity. Conversely, upregulation of IRS2 protein or increasing its signaling potential or blocking pathways that inhibits its function correct these problems, which prevents or cures the key pathologies of type 2 diabetes.

Drugs that increase IRS2 expression in mice stimulate beta cell function. An example of such a drug is exendin-4. Exendin-4 is a homolog of the natural peptide produced in the intestine called glucagon-like peptide-1. GLP1/Ex4 upregulates IRS2 levels in β-cells because they stimulate the production of cAMP. GLP1/Ex4 have similar effects in mouse and human islets to upregulate the levels of IRS2. Other drugs that increase cAMP levels in these and other cells also increase IRS2 levels and stimulate its signaling pathways. Many of the positive actions of GLPL1/Ex4 on mouse and human cells are prevented by blocking the IRS2 gene from expressing its IRS2 protein product.

Thus upregulation of IRS2 function is a treatment for type 2 diabetes and other diseases in which dysregulated insulin signaling is a component, such as obesity, dyslipidemia, hypertension, cardiovascular disease, Alzheimer disease, neurodegemeration, stroke, blindness, kidney disease, female infertility, and angiogenesis disorders. Conversely, reduction of IRS2 function can be used to treat metastatic disorders (e.g., neoplastic diseases and cancer).

By upregulation of IRS2 function is meant an increase in the amount of IRS2 protein within a cell or enhancing IRS2-mediated signal transduction by activators as defined herein. By activator or inhibitor of IRS2 is meant a small molecule that binds to IRS2 alone and activates or inhibits the signaling function of IRS2, or a small molecule that binds to a complex comprising IRS2 and other cellular proteins and wherein said small molecule cannot bind to the non-IRS2 proteins in the absence of IRS2. By reduction or downregulation of IRS2 function is meant a decrease in the amount of IRS2 protein within a cell or reduced IRS2-mediated signal transduction by inhibitors as defined herein.

There are three important elements of the invention disclosed herein which may be described as follows:

1. The key concept pertains to modifying (i.e., stabilizing or inhibiting) the IRS2 binding interaction with various proteins both upstream and downstream that interact with (bind to) IRS2. These include, for example, the human Insulin Receptor (HIR) which binds to and phosphorylates IRS2, the N-terminal c-jun kinase (JNK), PKC isoforms, ERK1 or ERK2, as well additional upstream or downstream signaling elements such as src homology 2 (SH2) domain-containing proteins that bind to IRS2 and may also phosphorylate, dephosphorylate or otherwise modify IRS2.

2. The specific pattern of covalent modifications of IRS2 such as phosphorylation of serine, threonine and tyrosine residues, ubiquitination patterns, or other covalent modifications that alter the function, intracellular localization, or stability of IRS2.

3. Methods that control the expression of the IRS2 gene in specific cells, including beta cells, brain cells, liver cells muscle cells, reproductive cells and tissues involved in reproduction, fat cells, mammary cells, bone cells and immune system cells, essentially any cells of the body where IRS2 might be naturally or unnaturally expressed.

Accordingly, methods of restoring or enhancing insulin sensitivity and/or pancreatic β-cell function depend on increasing IRS2 function by any means, particularly those listed above. Thus, IRS2 function is increased by increases in the amount of IRS2 protein in a cell, by modulation of specific interactions between IRS2 and other cellular components that modify IRS2, and by modulation of IRS2 interaction with its substrates.

Although certain of these effects may be opposite in nature depending upon the cellular context, such modulations may be achieved pharmacologically with compounds, (and especially small molecules), that either stabilize IRS2 interactions with other proteins or accelerate the "off" rate of such interactions after IRS2 has interacted with said proteins. Depending upon the cellular context, any of the aforementioned activities will lead to alterations in cellular functioning of the IRS2-mediated signal transduction cascades, resulting in improvements in cellular signaling relevant to the disease states of interest as will be discussed in detail below.

The method involves up regulating the expression or functional cellular activity of IRS2, and preferably with respect to IRS1 or other IRS family members or other proteins. Up regulation of the IRS2 gene or IRS2 protein function promotes cell and tissue functions particular to the specific target tissue. Methods that promote IRS2 signaling, by up regulating IRS2 expression or IRS2 function in specific tissues can target or prevent specific diseases involving those specific tissues or cells. For example, up regulation of IRS2 in pancreatic α-cells improves glucose stimulated insulin secretion. Drugs that up regulate the IRS2 gene or promote IRS2 signaling in β-cells will promote β-cell function and prevent or cure diabetes. Further, the level or functional activity of IRS2 can be modulated in human beings and other mammals in order to ameliorate or even prevent the failure or massive destruction of pancreatic β-cells that causes certain forms of diabetes, and reduce the need for insulin by peripheral insulin sensitive tissues.

IRS2 is also important in peripheral tissues that respond to insulin, so up regulation of the IRS2 gene or up regulation of IRS2 signaling function makes tissues more sensitive to insulin and thus less insulin is needed to elicit the appropriate response. In one embodiment two or more different drugs might be developed that promote IRS2 gene expression or IRS2 function in β-cells or in hepatocytes or in neurons. Alternatively, a single compound might promote IRS2 gene expression or IRS2 signaling and function in all of these tissues. These effects of IRS2 work together to keep glucose under control and prevent diabetes and related disorders that are modulated by IRS2 function.

In another example, up regulation of IRS2 expression or an increase of IRS2 signaling function can also be beneficial to other tissues. For example, approximately half of the growth of a mouse brain depends on the expression of the IRS2 gene. Therefore, drugs that promote IRS2 signaling will also be expected to promote brain growth in mammals and people. IRS2 signaling also plays a role in dephosphorylation of the Tau protein, a marker of Alzheimer disease. Up regulation of IRS2 in the hippocampus should promote normal function and contribute to the prevention of the neuronal degeneration associated with Alzheimer disease.

IRS2 signaling also plays a role in feeding behavior and female fertility. Mice lacking IRS2 tend to gain weight as a result of the inability of the brain to properly assess whether insulin has been secreted or not after a meal, so the brain can not determine whether a meal has in fact been consumed. Upregulation of IRS2 in the hypothalamus, and particularly the arcuate nucleus of the hypothalmus, will promote appetite regulation that results in reduced weight gain or even weight loss The invention further comprises methods to discover and utilize compounds that upregulate the function or levels of IRS2 in people to prevent or cure diseases associated with insulin resistance syndrome, especially diabetes.

In another embodiment, the invention can be used to determine whether known drugs already in use for the treatment of other diseases also promote IRS2 signaling functions or up regulation of IRS2 gene expression. This would reveal new mechanisms of action for old drugs that might indicate their use in human diseases caused by failure of the IRS2 signaling system, such as insulin resistance, diabetes and the complications resulting from these disorders.

IRS2 promotes growth of the retina. Mice lacking IRS2 display increased loss of retinal neurons, especially rod and cones, leading to blindness. Thus, upregulation of IRS2 or increased IRS2 is useful for reducing or preventing retinal degeneration and promoting retinal growth and regeneration.

Assay Systems for Identification and Subsequent Use of Modulators of IRS2 Function.

Cell-based assay systems capable of being adapted specifically for the examples which follow below have been previously developed by Applicants (See, for example, U.S. Pat. No. 5,688,655). Furthermore, certain cell-free assay systems are also useful for identifying compounds as discussed in detail in the examples given below. One such cell-free system consists of an electrochemiluminescence methodology whereby protein-protein interactions may be measured by the emission of light at a specific wavelength when the IR interacts with (i.e. binds to) IRS2. Such cell free assay systems are also capable of being utilized in the identification and characterization of compounds as discussed in detail in the examples given below. Other examples are well known to investigators of skill in the art.

Methods of Identifying and Using Compounds that Inhibit the Degradation of IRS2 in β-Cells.

In the most general approach, cell-based screens can be established to identify compounds that block the intracellular degradation of IRS2. Although a variety of cell types can be used for this process, one that expresses (or overexpresses) IRS2 would be preferable, for example, according to prior teachings of U.S. Pat. No. 5,688,655 and related patents. For example, ubiquitination promotes degradation of both IRS1 and IRS2. Therefore, certain drugs that inhibit ubiquitination would be anticipated to protect cells from the deleterious effects that result from the loss of IRS2 and can be identified using cell-based screens. Also, engineering an IRS2 cDNA for the purpose of detecting degradation of IRS2 would also be useful. This may be performed, for example, through the addition of a flag tag at the COOH end of the molecule. Such tags include a FLAG tag, GFP tag, a MYC tag, and others known to those of skill in the art.

Methods of Identifying and Using Compounds that Upregulate IRS2 Function in β-Cells.

Another way to upregulate IRS2 expression is by a substance that stimulates transcription of the IRS2 gene. This can also be performed with the cell based screening methods described above. β-cell lines, such as Min6, can be prepared with an IRS2 promoter linked to an easily detectable reporter such as a green fluorescence protein (GFP) to facilitate high throughput screening. PCR based screening methods may also be used to directly detect the expression of the endogenous gene. The hits can be tested for function on isolated mouse or human islet cells. Tissue specificity of the hits can be tested across various cell lines to determine whether the identified compounds are specific for β-cells or also promote IRS2 expression in other cells. GLP1 or exendin4 can be used as positive controls in such an assay to validate the assay.

Upregulation of IRS2 in Beta Cells and Other Tissues Using Glucagon Like Peptide 1 (GLP-1).

GLP-1, as well as stable analogs like Exendin-4, has been suggested as potential treatments for diabetes because they appear to promote insulin secretion in response to increases in plasma glucose levels. GLP-1 has been shown to reverse the age-dependent decline in β-cell function in rats or mice. Furthermore, GLP-1 also stimulates β-cell proliferation and neogenesis, and reduces or eliminates apoptosis of β-cells. GLP-1 secretion has also been shown to decrease in people with Type 2 diabetes, whereas subcutaneous administration of GLP-1 is able to improve glucose homeostasis, lower body weight, reduce circulating plasma free fatty acid and hemoglobin A(1C) and increase cellular responsiveness to insulin. GLP-1 strongly up regulates IRS2 in beta cells and other cells. Many of the positive effects of GLP-1 on beta cells function are lost upon inhibition of IRS2 expression, demonstrating that IRS2 plays an important role in GLP-1 action (FIG. 1). Interestingly, attempts to restore normal glucose homeostasis in IRS2 mice by the administration of Exendin-4 by injection were unsuccessful.

Compounds and Methods of Using GLP-1 Analogs that Upregulate IRS2 in Beta Cells.

Since GLP-1 promotes expression of IRS2, small molecules (i.e. chemical agents with molecular weights less than or equal to 1,000 atomic mass units (Daltons)) that are chemical analogues of GLP-1 or other chemical agents capable of activating the GLP-1 receptor will also be able to increase IRS2 expression. Such chemical compounds will preferably be orally available and can be used to promote IRS2 expression in β-cells and other cells that contain GLP-1 receptors. By definition, substances capable of upregulating IRS2 function are small molecules that increase the level of IRS2 protein capable of functioning within a cell as well as activators of IRS2 as defined herein.

Compounds and Methods of Using Cyclic AMP Modulators to Upregulate IRS2 in Beta Cells and Other Tissues.

Drugs that upregulate the concentration of cAMP in cells are well known. Since IRS2 expression is modulated in part by cAMP levels in some cells, many current drugs may exert some of their effects by functioning through the upregulation of IRS2. Thus, evaluating known drugs for specific effects on IRS2 expression in tissues will reveal new uses of the known drugs for the treatment of disease related to the loss of IRS2 expression or cellular function. Some of the effects of certain known drugs may be dependent upon their ability to upregulate IRS2. Cell-based assays based on IRS2 expression or reporter constructs can be used to evaluate known drugs or identify new compounds that upregulate IRS2 expression or protein synthesis.

Methods of Identifying and Using Compounds that Upregulate IRS2 in a Tissue-Specific Manner to Prevent Diseases of Insulin Resistance Syndrome.

A drug that upregulates IRS2 might work on all tissues of the body, or display tissue specificity. The effect(s) of known and unknown drugs on tissue-specific expression of IRS2 can be assessed. As known to one of skill in this art, one method to do this is to construct a mouse that expresses an IRS2 construct containing a carboxy terminal (COOH) extension comprising green fluorescent protein. After administration of compounds to the test animal, all tissues can be evaluated for expression of the tagged IRS2 protein to establish the tissue-specific effects of the particular compound with respect to the expression of the IRS2 gene.

Methods of Identifying and Using Compounds that Stimulate Signaling by IRS2 in β-Cells and Other Cell Types.

IRS2 signaling is inhibited by many pathways including degradation and serine phosphorylation (FIG. 1). Compounds that inhibit these processes will upregulate IRS2 function. As discussed previously, a general cell based assay system can be set up to identify compounds that increase IRS2 signaling. Various experimental strategies may be used to determine when such drugs are identified, including glucose uptake by the cell or the subsequent expression of other known downstream genes. The effect of the compounds on the ability of insulin to modulate gene expression (for example, in cells capable or incapable of expressing IRS1 or IRS2) can be further determined. If a known set of genes are selected for this purpose, reporter constructs can be developed and expressed in test cells. Alternatively, the entire genome can be used to assess the effects of the compounds on these cells, in which case microarray technology can be employed.

Inhibitors of Serine Phosphorylation of IRS2.

Serine phosphorylation sites are known to modulate the activity of IRS1 and IRS2 function. Compounds that inhibit or stimulate phosphorylation of the serine residues can be identified and these used to promote IRS2 function and prevent diabetes, the complications of diabetes or the insulin resistance syndrome, or other disorders in which IRS2 function plays a role as discussed previously. A proteomic approach can be developed to evaluate the phosphorylation of the relevant serine residues. One approach could use antibodies that specifically recognize and bind to phosphorylated serine residues in specific defined sequence motifs. Specific antibodies can be generated in rabbits or in mice (polyclonal or monoclonal) and arrayed in such a way as to evaluate all the residues simultaneously in cell extracts exposed to test compounds.

Introduction of an Artificial IRS2 Gene into β-Cells to Upregulate IRS2 Expression.

Gene therapy is a general method for correcting errors in gene expression in various cells. An artificial gene encoding IRS2 can be introduced in to β-cells to increase the expression of IRS2 and prevent diabetes. The gene can be constitutively active or it might contain regulatory elements that control its expression. Viral vectors (adenovirus, HIV, lentivirus) and other delivery systems methods are available for transfection and upregulation of IRS2 in β-cells or other cells of the body. The upregulation of the IRS2 gene might be accomplished during incubation of isolated human islets immediately after isolation from human donors. These islets that are engineered to express IRS2 can then be used for transplantation. Upregulation of IRS2 in murine islets promotes their function during transplantation, resulting in, for example, improved efficacy of transplants and reduction in the number of cells required.

Introduction of a Regulatory Sequence that Targets and Upregulates the Endogenous IRS2 Gene in β-Cells.

Gene expression is regulated by regulatory elements that bind various transcription factors. Regulatory elements may be substituted or added to modify IRS2 gene expression. For example, regulatory elements that increase expression or that respond to other signaling systems can be used. Various strong promoters are available that can be inserted in front of IRS2 to increase expression. Such elements can be targeted to cells in a cell type- or tissue-specific manner.

Introduction of an Artificial IRS2 Gene into Isolated β-Cells or Pluripotent Stem Cells for Implantation into Patients.

Islet cells can be removed from the body and treated with DNA that will alter the expression of the IRS2 gene, such as by introducing additional copies of IRS2, or by altering the regulatory region of IRS2 by homologous recombination. These engineered cells can then be replaced into the body to cure diabetes. Alternatively, islet cells can be obtained from other sources (e.g., matched donors), expression of IRS2 upregulated by altering the expression of the gene by the methods described above and the cells can be replaced in the patient. In another approach, islet cells can be differentiated from isolated stem cells. Islets cells can also be obtained from other mammals (e.g., pigs, cows, primates) and expression of IRS2 increased by genetic means as described above. The islet cells can be modified so as to be acceptable for human transplantation, or placed into an appropriate biocompatible container to avoid rejection.

Introduction of an Artificial IRS2 Gene into Neurons that are Subsequently Put Back into Patients.

IRS2 is highly expressed in specific regions of the brain, including the hypothalmus, hippocampus, amygdala and cortex. IRS2 promotes neuronal growth and inhibits the phosphorylation of Tau, a marker of Alzheimer's disease. IRS2 also promotes growth of CNS neurons during development. Upregulation of IRS2 expression in cells used to repair neuronal damage can significantly enhance the opportunity for repair and the production of neurotransmitters. Introduction hippocampal neurons expressing IRS2 into a hippocampus might prevent Alzheimer disease in susceptible individuals. Neurological damage in general, caused by trauma, might be repairable by introducing neurons into the damaged area for repair. The repair might be more likely to succeed if the neurons used contain elevated levels of IRS2 expression. Elevated IRS2 expression can be achieved by genetic manipulation or pharmaceutically active agents as outlined above.

Methods of Identifying and Using Compounds that Inhibit Degradation of IRS2 in β-Cells.

IRS2 is sensitive to proteolytic degradation. Accordingly, protease inhibitors can be used to upregulate IRS2 signaling potential by interfering with degradation of IRS2. Cell based or cell-free screening assay systems (as previously described) screens can be used to identify such inhibitors.

Methods of Identifying and Using Compounds that Block the Interaction of IRS2 with Degrading Enzymes in β-Cells and Other Cell Types.

Specificity is frequently achieved in biological systems through specific protein-protein interactions. In the case of enzymes that promote degradation of IRS2, compounds that prevent the specific interaction between IRS2 and the degradation enzymes would result in the upregulation of IRS2 protein. Cell-based and cell-free screens can be designed using tagged proteins to identify proteins that prevent the interaction of IRS2 with degradation enzymes.

Enhancement of Fertility.

Female mice lacking IRS2 are infertile. By upregulating IRS2 signaling or IRS2 gene expression in ovaries, ovulation may be enhanced.

Methods of Identifying and Using IRS2 Promoting Compounds to Reverse Catabolism During Acute Trauma.

Insulin resistance is a major problem during acute trauma. Decreased insulin secretion during acute trauma exacerbates the problems. Insulin resistance and decreased insulin secretion leads to massive catabolism that can threaten survival in the early period of repair. Both processes can be explained by the loss of IRS2 signaling due to inhibition by inflammatory processes. Drugs that promote IRS2 function, prevent IRS2 degradation, or promote IRS2 expression will reverse these effects.

Methods of Identifying and Using IRS2 Promoting Compounds to Prevent Insulin Resistance and Diabetes Associated with Obesity.

A major problem with obesity is that peripheral tissues become insulin resistant; if β-cells fail to make enough insulin to overcome the insulin resistance then diabetes develops. This can be treated with compounds that upregulate IRS2 in β-cells and/or peripheral tissues. Upregulating IRS2 in β-cells promotes better glucose detection and insulin secretion, and upregulating IRS2 in peripheral tissues reduces the insulin requirements. Accordingly, the incidence of life threatening complications of obesity can be reduced.

Regulation of Genes that Modulate IRS2 Levels and Function in β-Cells and Other Cell Types.

Like other genes, IRS2 is regulated by transcription factors such as CREB. One way to increase IRS2 expression is to increase the activity of the transcription factors that stimulate the transcription of the IRS2 genes. Such compounds can be easily identified through the use of cell based screens, as previously described. In particular, cells can be engineered to express IRS2 reporter genes and high or low levels of CREB. Substances that up regulate the IRS2 reporter can then be identified by measuring the differential responses of the compounds in cells expressing high or low levels of CREB.

Identification of Compounds that Activate or Inhibit Components of the IRS2 Signaling Cascade.

Figure 2:
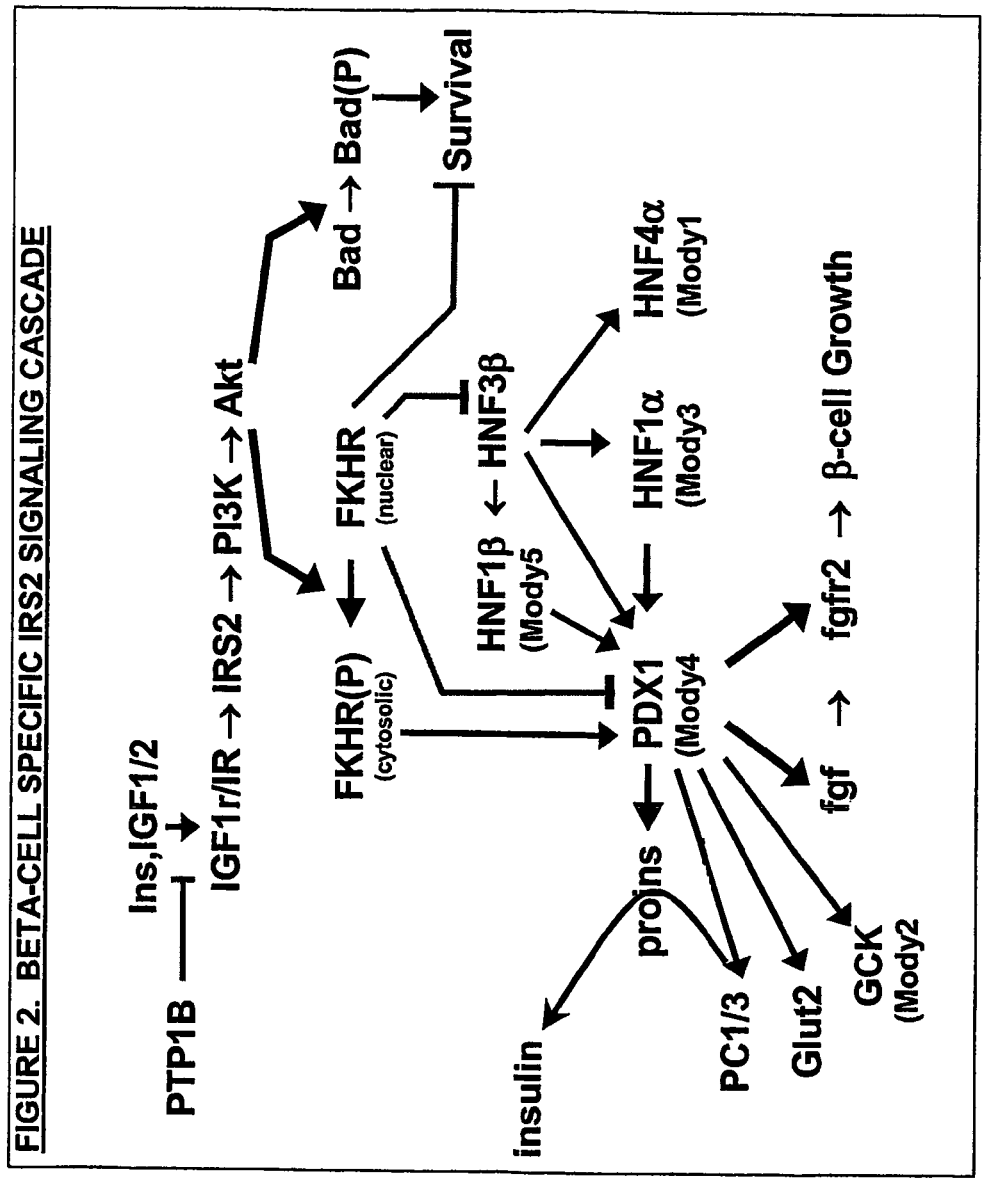
FIG. 2 depicts aspects of the IRS2 signaling cascade that are specific to β-cells.

IRS2 is an early component in a signaling cascade that controls cellular events and gene expression (FIG. 1). Many other components of the pathway are known. Accordingly, reduced activity of IRS2 may be compensated by modulating activity of downstream components. For example, genetic deletions of pTEN, Foxo1 or PTP1B, all of which inhibit IRS2 signaling, compensate for the lack of IRS2 and promote β-cell function in mice. Accordingly, substances that inhibit these components can stimulate IRS2 signaling pathways. Such drugs can be identified by cell based or purified protein-based assays. Similar strategies can be applied to other elements in the cascade (FIGS. 1 and 2).

Methods of Identifying and Using Compounds that Suppress Inhibition or Destruction of IRS2 in β-Cells by the Immune System.

Type 1 diabetes is an autoimmune disease. Leukocytes are attracted to islets by β-cell autoantigens. Once they have migrated to pancreatic islets, the leukocytes then attack and destroy β-cells through cell-cell contacts or by releasing proinflammatory cytokines that promote β-cell death. Death of a β-cells is thought to occur through mechanisms that are common to other cells, such as activation of the caspase cascade including the cleavage and activation of caspase-3. IRS2 signaling generally inhibits apoptosis of many cells types, including β-cells, by promoting phosphorylation of BAD and dissociation of BCL1 that inhibits a cascade that culminates in caspase-3 cleavage and activation. One of the ways that leukocytes prepare cells for rapid killing by promoting degradation of IRS2 or inhibiting its function. Compounds that inhibit degradation of IRS2 and inhibit its serine phosphorylation will oppose the killing effects of leukocytes. These compounds can be identified by establishing cell based assays performed in the presence of proinflammatory cytokines. Compounds that upregulate IRS2, stabilize it, promote its function or block its interaction with proteins in the inflammatory cascades will promote β-cell survival and function that can be assayed with standard tools.

Methods and Compounds that Protect the Tyrosine Phosphorylation State of IRS2 in β-Cells.

IRS2 mediates signals that promote functional growth and survival of β-cells through tyrosine phosphorylation mediated by the IGF1 receptor, insulin receptor or other receptors coupled to tyrosine kinases. Phosphatases dephosphorylate IRS proteins and inhibit these positive effects. Compounds that inhibit specific phosphatase activities in β-cells will upregulate IRS2 function and promote β-cell function. General screening methods are well known that can be used to find drugs with the proper phosphatase inhibiting effects. For example PTP1B is an example of one such phosphatase that can be targeted for inhibition, and there are other important phosphatases in β-cells as well as in other cell types.

Methods and Compounds that Inhibit Ubiquitination of IRS2 in β-Cells.

IRS2 proteins are targeted for degradation upon ubiquitination. Therefore, compounds that inhibit the interaction between IRS2 and ubiquitin transferase complexes or inhibit the accessibility of residues that get ubiquitinated will prolong the half life of IRS2 and thereby enhance is signaling capacity.

Methods and Compounds that Activate or Inhibit Serine, Threonine and Tyrosine Phosphorylation of IRS2 in β-Cells, Neurons, and Other Cell Types that are IRS2 Sensitive for Growth, Function or Survival.

IRS2 proteins are targets for phosphorylation by serine, threonine and tyrosine kinases. Therefore, compounds that inhibit or stimulate phosphorylation of IRS2 will modulate IRS2 cellular function in a therapeutically useful manner. Such functions of IRS2 will include its ability to interact with (bind to) other proteins involved in various signal transduction cascades that are beneficial for the treatment of human diseases such as type 2 diabetes, neurodegenerative diseases such as Alzheimer's disease, cardiovascular diseases, peripheral neuropathy, vascular disease, retinopathies, macular degeneration, and the like.

In the present invention, a therapeutically effective amount of one or more compounds that modulate IRS functional activity is administered to a mammal in need thereof. The term "administering" as used herein means delivering the compounds of the present invention to a mammal by any method that may achieve the result sought. They may be administered, for example, orally, parenterally (intravenously or intramuscularly), topically, transdermally or by inhalation. The term "mammal" as used herein is intended to include, but is not limited to, humans, laboratory animals, domestic pets and farm animals. "Therapeutically effective amount" means an amount of a compound that, when administered to a mammal, is effective in producing the desired therapeutic effect, such as inhibiting kinase activity.

Suitable carriers include, for example, one or more of water, saline, phosphate buffered saline, dextrose, glycerol, ethanol and the like, as well as combinations thereof. Carriers can further comprise minor amounts of auxiliary substances, such as wetting or emulsifying agents, preservatives or buffers, which enhance the shelf life or effectiveness of the binding polypeptides. The compositions can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions of the present invention are prepared in a manner well known in the pharmaceutical art. In making the composition the active ingredient will usually be mixed with a carrier, or diluted by a carrier and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing, for example, up to 10% by weight of the active compound, soft and hard gelatin capsules, suppositories, injection solutions, suspensions, sterile packaged powders and as a topical patch.

It should be appreciated that the methods and compositions of the present invention can be administered to any suitable mammal, such as a rabbit, rat, or mouse. More preferably, the mammal is a human.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The examples which follow further illustrate the invention, but should not be construed to limit the scope in any way.

EXAMPLES

The knockout of IRS2 shows that insulin action and secretion are closely linked at the molecular level through the insulin receptor substrate-2 (IRS2) branch of the insulin/IGF signaling cascade. Mice lacking IRS2 display similarities to humans with type 2 diabetes. The actions of β-cell-specific overproduction of IRS2 on diabetes development and pancreatic β-cell function in murine models of autoimmune diabetes and islet transplantation were evaluated. (Hennige, A. et al., J. Clin. Invest. 112:1521-1531 (2003)). M. White and colleagues showed that upregulation of IRS2 in pancreatic β-cells promotes β-cell growth, survival, and insulin secretion. Furthermore, they demonstrated that increased expression of IRS2 in β-cells improves islet transplantation, as significantly fewer islets were required to normalize serum glucose levels. The data support a pharmacological role for IRS2 or downstream factors in the treatment of β-cell failure and human diabetes. The results provide support for the teachings of the present invention that one way to realize the goal of preventing or curing diabetes and related metabolic disorders is to identify compounds that increase the activity or function of IRS2 in β-cells, or in other tissues of the body that require the IRS2 signaling function including brain or specific neuronal tissues like retina, hypothalamus, hippocampus, amygdala; heart, liver, muscle, adipose, ovary, pituitary, leukocytes, retina, or other cells or tissues that respond to insulin or IGF1 by generating signaling cascades that are coordinated by IRS2.

Jhala et al. (Genes Dev. 17:1575-1580 (2003)) provides evidence that IRS2 is a CREB responsive gene, and that GLP1/ex4 strongly increases IRS2 expression in β-cell lines, presumably through cAMP mediated phosphorylation of CREB. By contrast, IRS expression is not regulated through activation of CREB. The results demonstrate that compounds exist that can upregulate the synthesis of IRS2 in cells, and particularly with respect to another IRS protein, and that compounds that increase cAMP levels in cells, including cell surface receptor agonists, phosphodiesterase inhibitors, PKA activators, and cAMP mimetics, can also upregulate IRS2 through activation of Creb.

Accordingly, these results taken together with the teachings of the invention described herein provide additional evidence that IRS2 synthesis can be increased in a specific manner in β-cells to prevent or cure diabetes.

We claim:

1. A method of determining whether a small molecule is an activator or an inhibitor of insulin receptor substrate 2 (IRS2) which comprises:
   a) providing a test cell which overproduces IRS2 and exhibits an increase in binding of an IRS2-binding protein to IRS2, relative to a control cell which produces IRS2 at a lower level, or does not produce the protein at all, and which exhibits a lesser amount of binding of said protein to IRS2;
   b) causing the small molecule to come into contact with IRS2 or a complex comprising IRS2 and an IRS2-binding protein in the cell; and
   c) examining the test cell for modulation of an IRS2-mediated cellular signal, wherein the modulation is greater in the test cell as compared to the control cell, thereby identifying the small molecule as an activator or an inhibitor of IRS2.

2. The method of claim 1, wherein the test cell is obtained by introducing a nucleic acid encoding insulin receptor substrate 2 (IRS2) into a host cell, said nucleic acid being under the control of a promoter functional in the host cell, whereby said nucleic acid is expressed.

3. The method of claim 1, wherein the nucleic acid is introduced into the test cell by means of a genetic vector into which the gene has been inserted.

4. The method of claim 1, wherein the nucleic acid is introduced into the test cell by means of a retroviral vector.

5. The method of claim 1, wherein the control cell essentially does not produce insulin receptor substrate 2 (IRS2).

6. The method of claim 1, wherein the test cell is a myeloid cell.

7. The method of claim 6, wherein the test cell is an FDC-P1 cell.

8. The method of claim 1, wherein the modulation of an IRS2-mediated cellular signal is determined by measuring the effect on a component of the IRS2 signaling cascade.

9. A method of determining whether a small molecule is an activator or an inhibitor of insulin receptor substrate 2 (IRS2), wherein said activator or inhibitor binds to IRS2 or to a complex comprising IRS2 and an IRS2-binding protein and cannot bind to the non-IRS2 proteins in the absence of IRS2, which comprises:
   a) providing a test cell which overproduces IRS2 and exhibits an increase in binding of an IRS2-binding protein to IRS2, relative to a control cell which produces IRS2 at a lower level, or does not produce the protein at all, and which exhibits a lesser amount of binding of said protein to IRS2;
   b) causing the small molecule to come into contact with IRS2 or a complex comprising IRS2 and other cellular proteins in the cell; and
   c) examining the test cell for modulation of an IRS2-mediated cellular signal, wherein the modulation is greater in the test cell as compared to the control cell;
thereby identifying the small molecule as an activator or an inhibitor of IRS2.

* * * * *

UNITED STATES PATENT AND TRADEMARK OFFICE
CERTIFICATE OF CORRECTION

PATENT NO. : 8,557,512 B2  Page 1 of 1
APPLICATION NO. : 10/541263
DATED : October 15, 2013
INVENTOR(S) : Housey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1026 days.

Signed and Sealed this

Fifteenth Day of September, 2015

Michelle K. Lee
*Director of the United States Patent and Trademark Office*